United States Patent [19]

Sholder

[11] Patent Number: 5,340,361
[45] Date of Patent: Aug. 23, 1994

[54] IMPLANTABLE PACEMAKER HAVING ADAPTIVE AV INTERVAL ADOPTIVELY SHORTENED TO ASSURE VENTRICULAR PACING

[75] Inventor: Jason A. Sholder, Northridge, Calif.

[73] Assignee: Siemens Pacesetter, Inc., Sylmar, Calif.

[21] Appl. No.: 975,747

[22] Filed: Nov. 13, 1992

[51] Int. Cl.$^5$ ............................................. A61N 1/36
[52] U.S. Cl. ........................................ 607/24; 607/9
[58] Field of Search ................................. 128/419 PG

[56] References Cited

U.S. PATENT DOCUMENTS

| | | | |
|---|---|---|---|
| 4,429,697 | 2/1984 | Nappholz et al. | 128/419 |
| 4,554,921 | 11/1985 | Boute et al. | 128/419 |
| 4,712,555 | 12/1987 | Thornander et al. | 128/419 |
| 4,722,341 | 2/1988 | Hedberg et al. | 128/419 |
| 4,788,980 | 12/1988 | Mann et al. | 128/419 |
| 4,847,617 | 7/1989 | Silvian | 340/870 |
| 4,940,052 | 7/1990 | Mann et al. | 128/419 |
| 4,944,298 | 7/1990 | Sholder | 128/419 |
| 4,974,589 | 12/1990 | Sholder | 128/419 |
| 5,086,774 | 2/1992 | Duncan | 128/419 |
| 5,144,950 | 9/1992 | Stoop et al. | 128/419 |

OTHER PUBLICATIONS

McAreavey, Dorothea M. D. et al., "Altered Cardiac Hemodynamic and Electrical State in Normal Sinus Rhythm After Chronic Dual-Chamber Pacing for Relief of Left Ventricular Outflow Obstruction in Hypertrophic Cardiomyopathy," *THE AMERICAN JOURNAL OF CARDIOLOGY*, vol. 70, pp. 651-656 (Sep. 1, 1992).

Brecker, Stephen J. D. et al., "Effects of dual-chamber pacing with short atriobentricular delay in dilated cardiomypathy," *THE LANCET*, vol. 340, pp. 1308-1312 (Nov. 28, 1992).

Barold, S. Serge MD, BS, FRACP, "Cardiac Pacing in Special and Complex Situations," *CARDIAC PACING*, vol. 10, No. 4, pp. 573-591 (Nov. 1992).

Hochleitner, Margarete M. D. et al., "Long-Term Efficacy of Physiologic Dual-Chamber Pacing in the Treatment of End-Stage Idiopathic Dilated Cardiomyopathy," *THE AMERICAN JOURNAL OF CARDIOLOGY*, vol. 70, pp. 1320-1325, (Nov. 15, 1992).

Hochleitner, Margarete M. D. et al., "Usefulness of Physiologic Dual-Chamber Pacing in Drug-Resistant Idiopathic Dilated Cardiomyopathy," *THE AMERICAN JOURNAL OF cARDIOLOGY*, vol. 66, pp. 198-202 (Jul. 15, 1990,).

*Primary Examiner*—William E. Kamm
*Assistant Examiner*—Scott M. Getzow
*Attorney, Agent, or Firm*—Malcolm J. Romano; Lisa P. Weinberg

[57] ABSTRACT

A dual-chamber implantable pacemaker configured to operate in the DDD or DDDR mode automatically adjusts its AV (or PV) interval to an amount just less than the natural conduction time of a patient, thereby assuring that ventricular pacing occurs in a patient's cardiac cycle at a time near when a natural ventricular contraction (an R-wave) would occur. The pacemaker includes a pulse generator that generates ventricular stimulation pulses (V-pulses) at the conclusion of a pacemaker-defined AV (or PV) interval if no natural ventricular activity (an R-wave) is sensed during such AV (or PV) interval. The AV (or PV) intervals are automatically adjusted by the pacemaker to be just less than the natural conduction time sensed by the pacemaker, where the natural conduction time is the time between atrial activity (a sensed P-wave or a delivered A-pulse) and the subsequent natural ventricular activity (R-wave). The system and method are particularly adapted for use by patients suffering from a cardiomyopathy in order to improve cardiac output.

34 Claims, 5 Drawing Sheets

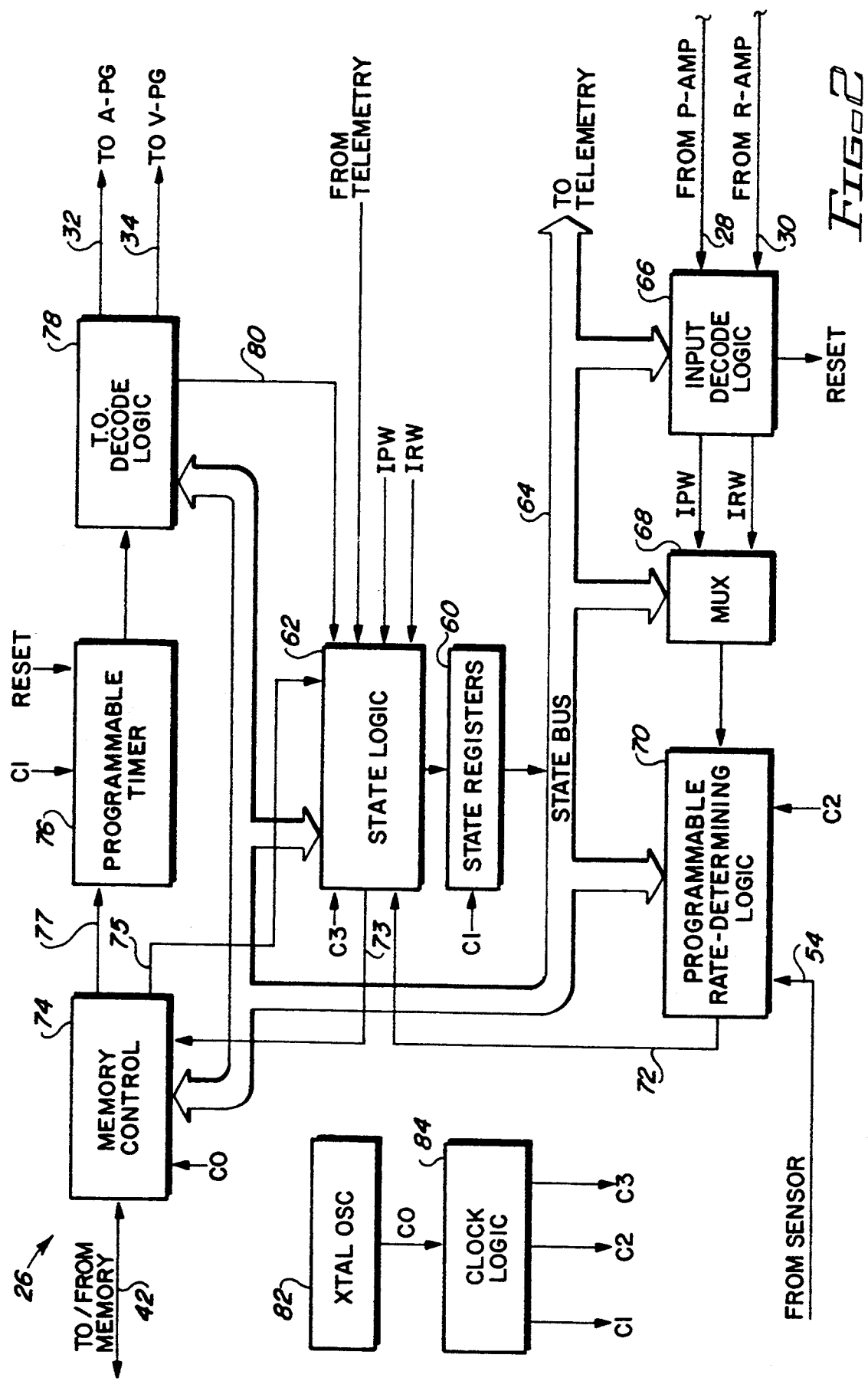

IMPLANTABLE PACEMAKER HAVING ADAPTIVE AV INTERVAL ADOPTIVELY SHORTENED TO ASSURE VENTRICULAR PACING

BACKGROUND OF THE INVENTION

Field of the Invention

The present invention relates to implantable medical devices and methods, and more particularly, to an implantable pacemaker that automatically adapts its atrial-ventricular (AV) delay to maximize the cardiac output for patients having a cardiomyopathy.

The heart is a pump that pumps life-sustaining blood throughout the body of the patient. The human heart comprises a left side and a right side, with each side having a first chamber, known as the atrium, and a second chamber, known as the ventricle. The atrium receives blood returning from other body locations. At an appropriate time, determined by the sinoatrial (SA) node, an electrical stimulus is provided that causes the muscle tissue surrounding the atrium to depolarize. Depolarization of the atrial muscle tissue is manifest by the occurrence of an electrical signal known as the P-wave. Immediately following the P-wave, the atrial muscle tissue physically contracts, forcing the blood held in the atrium through a one-way valve into the ventricle. The SA node stimulus that caused the atrium to depolarize also travels to the ventricle through the atrioventricular (AV) node and the atrioventricular (AV) bundle. The AV node is a mass of modified heart muscle situated in the lower middle part of the right atrium. It receives the impulse to contract from the sinoatrial node, via the atria, and transmits it through the atrioventricular bundle to the ventricles. The AV bundle is a bundle of modified heart muscle fibers (Purkinje fibers) that pass from the AV node forward to the septum between the ventricles, where it divides into right and left bundles, one for each ventricle. The fibers thus transmit the SA node stimulus from the atria, via the AV node, to the ventricles. However, as the SA node stimulus travels through the AV bundle, it is delayed by an amount commensurate with the same time it takes the blood to physically flow from the atrium to the ventricle.

After the delay through the AV bundle, which delay may be referred to as the natural conduction time of the heart, the SA node stimulus arrives at the ventricular muscle tissue, causing it to depolarize. Depolarization of the ventricular muscle tissue is manifest by the occurrence of an electrical signal known as the R-wave (sometimes referred to as the QRS complex). Immediately following the R-wave, the ventricular muscle tissue physically contracts, forcing the blood held therein through one or more arteries to various body locations. In this manner, then, the heart "beats" or pumps blood by having the atria contract at a rate determined by the SA node, and after the natural conduction time, by having the ventricles contract. After a longer delay, when the atrium has refilled with blood returning from throughout the body, the process repeats.

The heart of a typical healthy patient may beat 60-70 times per minute when the patient is at rest. When the patient is undergoing significant physiological stress, as occurs, e.g., during physical exercise, the rate at which the heart beats, the "heart rate," increases significantly, e.g, up to 150-170 times per minute. The above-described process wherein the atria and ventricles sequentially depolarize and contract in order to pump blood, and get ready to depolarize again, is referred to herein as the "cardiac cycle." A given cardiac cycle thus includes one R-wave (or equivalent ventricular activity evidencing depolarization of the ventricles) and one P-wave (or equivalent atrial activity evidencing depolarization of the atria). The length of the cardiac cycle (which represents the period of the heart rate) may be measured as the time interval between successive P-waves or R-waves, although R-waves are usually used because they are easier to detect.

A pacemaker is an implantable medical device that monitors the activity of the heart for the occurrence of P-waves and/or R-waves, and steps in with electronically generated stimuli, when needed, to force the depolarization of the atria and/or ventricles. A pacemaker-generated stimulus that is delivered to the atrium is referred to herein as an "A-pulse." A pacemaker-generated stimulus that is delivered to the ventricle is referred to herein as a "V-pulse." Most pacemakers are configured to provide an A-pulse and/or V-pulse only if a prescribed period of time has elapsed without the occurrence of a P-wave and/or an R-wave, i.e., without the occurrence of natural heart beats.

The prescribed period of time used by the pacemaker between contraction of the ventricle and contraction of the atrium is generally referred to as the V-A Interval, or the atrial escape interval. For most dual-chamber pacemaker modes of operation, only if a P-wave does not occur during the atrial escape interval will the pacemaker step in at the conclusion of such interval and generate an A-pulse.

The prescribed period of time used by the pacemaker between contraction of the atrium and contraction of the ventricle is referred to as the A-V Interval, or sometimes it is called the "AV Delay." The pacemaker, for most dual-chamber modes of operation, generates a V-pulse only if the AV Delay elapses without the occurrence of an R-wave.

In the above-described manner, the heart is thus afforded as much time as possible to beat on its own before the electronically-generated stimuli of the pacemaker are delivered to the heart, causing it to beat at the rate set by the pacemaker.

Heretofore, most cardiac patients using a pacemaker have suffered from at least one of various cardiac conditions or diseases that affect either the ability of the SA node to maintain and sustain a satisfactory heart beat rate (hereafter "rate problems"), or the ability of the AV node or the AV bundle to conduct a suitable stimulus to the ventricle (hereafter "conduction problems"). Advantageously, both rate problems and conduction problems lend themselves well to a pacemaker solution because the underlying cardiac muscle tissue is in place and is capable of responding to the electronically-generated stimuli produced by the pacemaker.

Unfortunately, there remain a significant number of patients that suffer from one or more conditions that cannot be characterized as either rate problems or conduction problems. One such problem is known as hypertrophic cardiomyopathy. Another is known as dilated cardiomyopathy. While there are medical or clinical differences between these two forms of cardiomyopathy, for purposes of the present invention they may be considered the same problem, and will be referred to hereafter as simply "cardiomyopathy."

In general, a patient suffering from cardiomyopathy experiences a significant reduction in cardiac output because the heart muscle is unable to perform its function of contracting in response to the SA node stimulus. By "cardiac output," it is meant the ability of the heart to efficiently pump blood. Thus, a patient suffering from cardiomyopathy will generally not have as much blood pumped per heart beat (stroke volume) as may be needed. Cardiomyopathy patients are referred to as being moderately to severely symptomatic of low cardiac output syndrome. The only treatment for low cardiac output syndrome, up to now, has been heart transplantation. Disadvantageously, heart transplantation is not a viable solution for most patients. Not only are hearts suitable for transplant difficult and expensive to secure, but even when secured, a very dangerous and complicated surgery must follow in order to successfully perform the transplantation operation. What is thus needed is an alternative to heart transplantation for patients suffering from low cardiac output syndrome.

It has recently been proposed to implant a dual-chamber pacemaker in patients suffering from low cardiac output syndrome and to configure such pacemaker to provide PV or AV pacing. During PV or AV pacing, the pacemaker delivers a V-pulse to the ventricles a programmed delay after the occurrence of an atrial event, which atrial event could be either the occurrence of a P-wave or the delivery of an A-pulse. Advantageously, by forcing a ventricular contraction prior to the occurrence of an R-wave, i.e., prior to natural depolarization of the ventricles, the cardiac output of patients suffering from cardiomyopathies may be significantly improved. Such improvement appears to result because the ventricular stimulus—a V-pulse delivered by the pacemaker—is applied to the ventricular tissue at a different cardiac location (at the location of the ventricular lead tip electrode, which location is usually in the apex of the right ventricle) than is the natural stimulus when received through the SA node.

PV or AV pacing is only effective, however, when the V-pulse is delivered to the ventricular tissue before the occurrence of an R-wave, i.e., before the ventricular tissue depolarizes. As soon as the ventricular tissue depolarizes, it becomes refractory, and will not respond to a V-pulse, until such time as it repolarizes. It is thus necessary, if AV or PV pacing is to be used, to set the AV (or PV) interval of the pacemaker to a value that is less than the patient's normal conduction time. Unfortunately, heretofore, this requirement has forced the AV (or PV) interval to be set to very short values, i.e., between 80 and 120 msec, because during exercise (or other periods of physical activity or physiological stress) the patient's native conduction time may shorten significantly. Thus, in order to guarantee that the pacemaker will always pace the ventricles, i.e., in order to assure that the V-pulse is delivered to the ventricular tissue at a time when it is not refractory, the AV (or PV) interval must be set to an interval that is shorter than any native conduction interval that might exist in any given patient at any given time.

Disadvantageously, setting a very short programmed AV (or PV) interval may adversely affect cardiac output because it may force ventricular contraction well before the ventricles have had sufficient time to be filled with blood from the atrium. Thus, what is needed for patients suffering from a cardiomyopathy is a pacemaker that paces the ventricles at a time in the cardiac cycle that is always less than the natural conduction time, i.e., at a time that is prior to the occurrence of an R-wave, but that is not so much less than the natural conduction time so as to adversely affect cardiac output. That is, what is needed is a pacemaker that automatically sets its internally-generated AV and/or PV intervals to be just short of the patient's native conduction time, thereby assuring that the AV (or PV) interval is sufficiently long to allow the blood to physically move from the atrium to the ventricles; yet remains sufficiently short to always be less than the patient's native conduction time, thereby assuring that the V-pulse is not delivered when the ventricular tissue is refractory.

The present invention advantageously addresses the above and other needs. See Applicant's copending application, filed concurrently herewith, entitled DUAL-CHAMBER IMPLANTABLE PACEMAKER HAVING AN ADAPTIVE AV INTERVAL THAT PREVENTS VENTRICULAR FUSION BEATS, Ser. No. 07/976,153, Attorney Docket No. GR 92P 7968, which application is incorporated herein by reference.

SUMMARY OF THE INVENTION

The present invention provides a dual-chamber implantable pacemaker and a method of operating such a dual-chamber implantable pacemaker, wherein the natural conduction time of a patient is measured, and the AV (or PV) interval of a dual-chamber pacemaker implanted in the patient is automatically set to a value just less than the measured natural conduction time. A ventricular stimulation pulse (V-pulse) is generated at the conclusion of the pacemaker-defined AV (or PV) interval if no natural ventricular activity (an R-wave) is sensed during such AV (or PV) interval. Because the AV (or PV) interval is automatically set to a value just less than the natural conduction time, a V-pulse will almost always be applied to the ventricular muscle tissue at a time when such muscle tissue is capable of responding thereto, i.e., at a time when the tissue is not refractory. In the event that an R-wave does occur, signaling that the natural conduction time of the patient is decreasing (as might occur, for example, if the patient is exercising), the occurrence of the R-wave provides a new measure of the natural conduction time, which thereafter affords a basis for further adjusting the AV interval.

The pacemaker-defined AV interval begins upon the delivery of an atrial stimulation pulse (A-pulse) by the pacemaker. Similarly, the pacemaker-defined PV interval begins upon sensing natural atrial activity (a P-wave) by the pacemaker. The natural conduction time measured by the pacemaker comprises the time between atrial activity (whether a sensed P-wave or a delivered A-pulse, whichever occurs) and subsequent natural ventricular activity (an R-wave). The method of operating a pacemaker in accordance with the present invention thus includes: (1) measuring the natural conduction time, $t_{AR}$, of the patient in a given cardiac cycle; and (2) setting the AV (or PV) interval of the pacemaker, for use in subsequent cardiac cycles, to a value that is a prescribed amount, e.g, 20–30 msec., less than $t_{AR}$.

In accordance with one aspect of the invention, the pacemaker includes a timing counter, or equivalent, that is initiated upon the occurrence of each atrial event, whether a P-wave or an A-pulse. The atrial event also starts the AV (or PV) interval of the pacemaker. If an R-wave occurs in the cardiac cycle before the termination of the AV (or PV) interval, then the timing counter stops, with the count held therein providing a measure of the natural conduction time, $t_{AR}$. The AV (or PV) interval set by the pacemaker is then immediately and automatically adjusted to a new value that is the prescribed amount less than $t_{AR}$. The new adjusted value of AV (or PV) is then used for the next cardiac cycle. In this manner, the AV (or PV) interval is adaptively adjusted, as required, to always be less than the natural conduction time of the patient.

In accordance with another aspect of the invention, if a prescribed number of consecutive cardiac cycles ensue without the occurrence of an R-wave, then the value of the AV (or PV) interval is gradually increased, in order to incrementally return it to its original value.

A dual-chamber pacemaker made in accordance with the present invention includes an atrial channel and a ventricular channel. An atrial sense amplifier senses the occurrence of natural atrial activity (a P-wave) in the atrial channel. A ventricular sense amplifier similarly senses the occurrence of natural ventricular activity (an R-wave) in the ventricular channel. An atrial pulse generator generates an atrial stimulation pulse (A-pulse) in the atrial channel in the absence of a sensed P-wave by the atrial sense amplifier within an AV time interval. Similarly, a ventricular pulse generator generates a ventricular stimulation pulse (V-Pulse) in the ventricular channel in the absence of a sensed R-wave by the ventricular sense amplifier within an atrial escape interval. A control circuit coupled to both the atrial and ventricular channels defines the AV time interval and the atrial escape interval. The AV time interval begins upon the sensing of atrial activity in the atrial channel, where atrial activity may be either a P-wave or the generation of an A-pulse, whichever event occurs. The atrial escape interval begins upon the sensing of ventricular activity in the ventricular channel, where ventricular activity may be either an R-wave or the generation of a V-pulse, whichever event occurs first. The control circuit of the pacemaker includes timing means for measuring a natural conduction time interval as the time period between atrial activity in the atrial channel and the sensing of an R-wave in the ventricular channel. In accordance with the present invention, the control circuit automatically decreases the AV time interval to a value that is less than the natural conduction time interval by a prescribed amount, which decreased AV time interval value is not to be less than a minimum AV time interval value.

Hence, in the absence of a decreasing natural conduction time interval, the pacemaker of the present invention generates a V-pulse in the ventricular channel prior to the occurrence of an R-wave, thereby providing needed therapy for patients who most always need a V-pulse, e.g., patients suffering from a cardiomyopathy. Further, in the presence of a decreasing natural conduction time interval, the pacemaker of the invention automatically decreases the AV time interval to a value that is less than the shortest conduction time interval.

Moreover, in accordance with one aspect of the invention, the control circuit of the dual-chamber pacemaker automatically increases the AV time interval by a prescribed amount in the event a prescribed number of consecutive cardiac cycles occur without an R-wave having been sensed by the ventricular sense amplifier. Thus, the AV time interval will never remain adjusted to a value less than the shortest conduction time interval in the absence of sensed R-waves for a period of time longer than the prescribed number of cardiac cycles. In this manner, then, the pacemaker adaptively adjusts its AV time interval, as required, between maximum and minimum values, always attempting to provide a V-pulse just prior to when an R-wave would otherwise occur.

It is thus a feature of the present invention to provide an implantable pacemaker and method of operating such a pacemaker that stimulates cardiac tissue at a time in the cardiac cycle that is just prior to when natural depolarization of the cardiac tissue would otherwise cause a cardiac contraction.

It is another feature of the invention to provide a dual-chamber pacemaker, and method of operating such a dual-chamber pacemaker, that automatically adjusts its pacemaker-defined AV interval to a value that is just less than the natural conduction time of a patient, thereby assuring that a V-pulse is generated and delivered to the ventricular muscle tissue at a time in the cardiac cycle when such ventricular muscle is not refractory (i.e., prior to the natural depolarization of the ventricular tissue), while still maintaining the approximate cardiac timing set by the natural conduction time, whereby the cardiac output of the patient is maximized.

It is a further feature of the invention to provide such a pacemaker, and method of operating such a pacemaker, that decreases the pacemaker-defined AV interval in response to sensing an R-wave (which sensed R-wave evidences a shortened natural conduction time), and that automatically increases the pacemaker-defined AV interval in prescribed increments in response to not sensing an R-wave for a prescribed number of consecutive cardiac cycles (which failure to sense any R-waves may evidence a lengthening of the natural conduction time).

BRIEF DESCRIPTION OF THE DRAWINGS

The above and other aspects, features and advantages of the present invention will become more apparent from the Detailed Description of the Invention, presented in conjunction with the following drawings, wherein:

FIG. 2 is a block diagram of one embodiment of the control logic of the pacemaker of FIG. 1;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention is directed to an implantable dual-chamber pacemaker, and a method of operating an implantable dual-chamber pacemaker, that automatically adapts or adjusts the AV interval (or PV interval) of the pacemaker in an attempt to maximize the cardiac output of a patient suffering from a cardiomyopathy. In general, the muscle tissue (usually the ventricular muscle tissue) of the heart of a patient suffering from a cardiomyopathy is unable to provide a strong beat (muscle contraction), and is thus not able to efficiently pump much blood with each beat. If a ventricular stimulation pulse (V-pulse) is provided to the heart at the right time in the cardiac cycle, then a stronger beat (muscle contraction) is provided, and the cardiac output (amount of blood pumped by the heart) of the patient increases. The "right time" to provide such a V-pulse in the cardiac cycle is just prior to when the ventricles would beat (depolarize, and hence contract) on their own due to the normal conduction time of the patient, i.e., just prior to the occurrence of an R-wave. To this end, the present invention determines the natural conduction time between a P-wave (evidencing depolarization of the atria) and a subsequent R-wave, or PR interval, and sets the PV interval of the pacemaker to be a prescribed amount less than such PR interval. Alternatively, should the atria of the patient also require stimulation, the invention determines the paced conduction time between an atrial stimulation pulse, (A-pulse) and a subsequent R-wave, or AR interval, and sets the AV interval of the pacemaker to be a prescribed amount less than such AR interval. In this manner, the pacemaker always delivers a V-pulse at the conclusion of the PV or AV intervals, which is less than the natural conduction time (PR or AR interval), and hence before the ventricles attempt to contract on their own.

Advantageously, the present invention may be implemented using a wide variety of dual-chamber pacemaker configurations and pacemaker hardware. Any pacemaker configuration that allows the pacemaker AV or PV intervals to be automatically set to a value that is a prescribed amount less than the AR or PR conduction-time intervals may be used to implement the invention. The description that follows is only exemplary of one such configuration.

Figure 1:
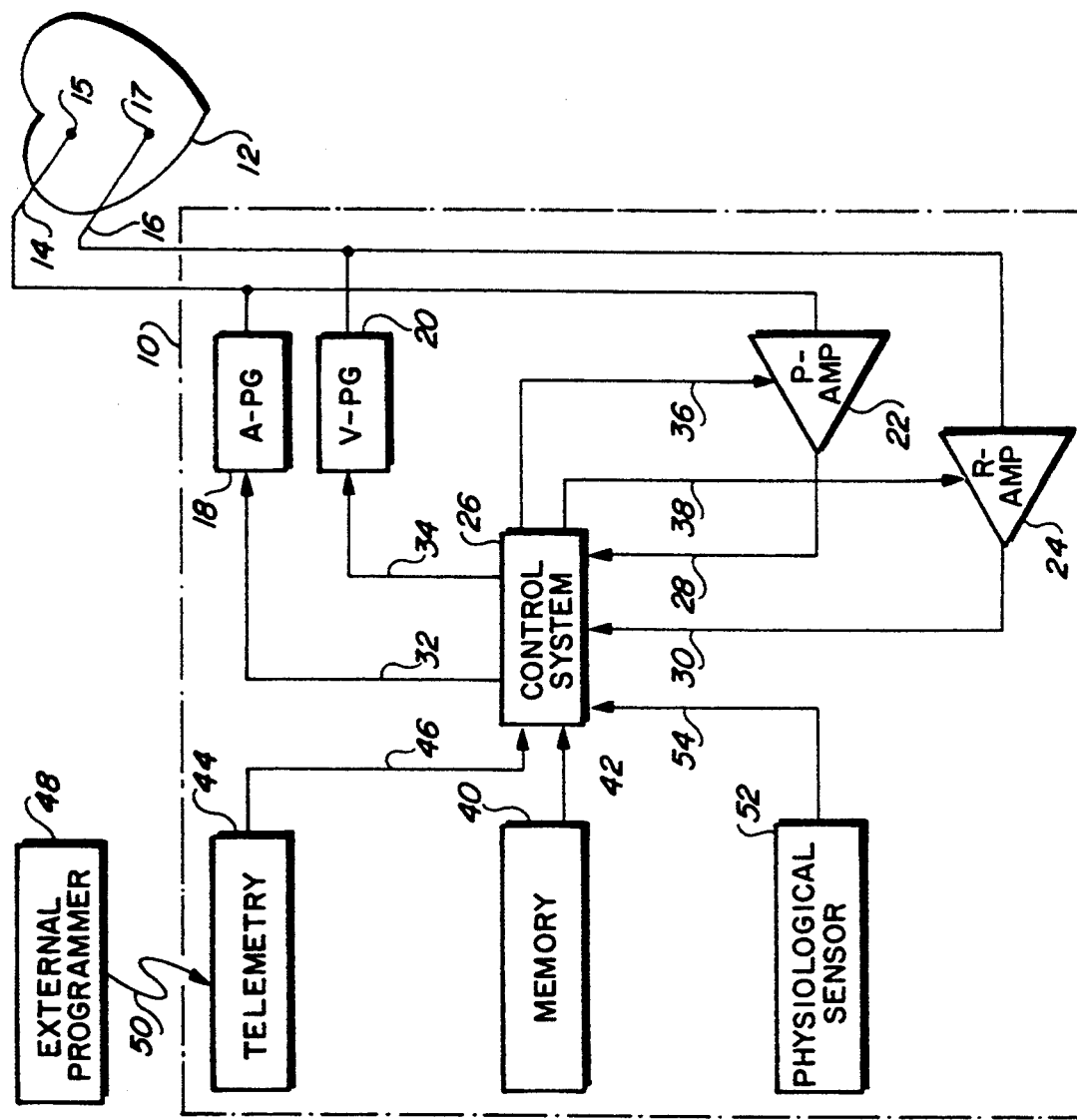
FIG. 1 is block diagram of a dual-chamber programmable pacemaker.

Referring then to FIG. 1, a block diagram of a dual-chamber pacemaker 10 is illustrated. The pacemaker 10 is coupled to a heart 12 by way of leads 14 and 16. The lead 14 has an electrode 15 that is in contact with one of the atria of the heart, and the lead 16 has an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

A control circuit or control system 26 controls the dual-chamber pacer 10. The control system 26 receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control circuit or system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. A stimulation pulse generated by the A-PG 18 is referred to as the "A-pulse," and the stimulation pulse generated by the V-PG 20 is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large A-pulse or V-pulse, respectively, that is present at the input terminals of such amplifiers during this time. Such blanking action also prevents the sensing of residual electrical signals that may be present in the muscle tissue as a result of the pacer stimulation, which sensing could falsely be interpreted as P-waves or R-waves.

Still referring to FIG. 1, the pacer 10 also includes a memory circuit 40 that is coupled to the control system 26 over a suitable data/address bus 42. The memory circuit 40 allows certain control parameters, used by the control system 26 in controlling the operation of the pacemaker, to be programmably stored and modified, as required, in order to customize the pacer's operation to suit the needs of a particular patient. Such data includes the basic timing intervals used during operation of the pacemaker, such as the programmed atrial escape interval (AEI). Further, data sensed during the operation of the pacer may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel. Advantageously, through the external programmer 48 and the communication link 50, desired commands may be sent to the control system 26. Similarly, through this communication link 50 and the programmer 48, data (either held within the control system 26, as in a data latch, or stored within the memory 40), may be remotely received from the pacer 10. In this manner, non-invasive communications can be established from time to time with the implanted pacer 10 from a remote, non-implanted, location. See, e.g., U.S. Pat. No. 4,847,617, issued to Silvian, entitled "High Speed Digital Telemetry System for Implantable Devices," incorporated herein by reference.

The pacer 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel.

In accordance with one embodiment of the present invention, the pacemaker 10 may further include one or more physiological sensors 52 that is connected to the control system 26 of the pacer over a suitable connection line 54. While the sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of sensors, such as physiologic sensors that sense the oxygen content of blood, respiration rate, pH of blood, and the like, may also be used in lieu of, or in addition to, an activity sensor. The type of sensor, if any, used is not critical to the present invention. Any sensor or combination of sensors capable of sensing body motion or a physiological parameter relatable to the rate at which the heart should be beating can be used. A pacemaker using such sensors is commonly referred to as a "rate-responsive" pacemaker because such a pacemaker adjusts the rate (escape interval) of the pacer in a manner that tracks the physiological needs of the patient.

Referring next to FIG. 2, a block diagram of one embodiment of the control circuit or system 26 of the pacer 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Threshold Adjustment." The '052 patent is assigned to the same assignee as is this application, and is incorporated herein by reference.

The control system shown in FIG. 2 is based on a state machine wherein a set of state registers 60 define the particular state of the pacer at any instant in time. In general, and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine, such as is described in the above-cited patent. The telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (Inhibiting P-Wave) and "IRW" (Inhibiting R-Wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal from the sensor 52 (FIG. 1), and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 2, a memory control circuit 74 provides the needed interface between the circuits of the control system 26 and the memory 40 (FIG. 1). This memory control circuit may be any conventional memory access circuit that sends or receives data to or from memory at a specified address. Data retrieved from memory 40 may be sent to either the state logic 62 (over signal line(s) 75) or to one or more programmable timers 76 (over signal line(s) 77). Data sent to memory 40 may be either the current state of the system (obtained off of the state bus 64), or other selected signals from the state logic (as made available over signal line(s) 78).

The programmable timer 76 defines a prescribed time interval, the length of which is set by the signal(s) received from the memory control 74 over signal line(s) 77, and the starting point of which begins coincident with the start of the current state, as obtained from the state bus 64. The timer 76 further generates a time-out (T.O.) signal when this prescribed time interval has elapsed. During the prescribed time interval, the timing function may be reset by a reset signal, typically obtained from the input decode logic 66, although some states (as obtained from the state bus 64) may also effectuate an immediate reset of the timer 76. The time-out signal is sent to time-out decode logic 78. It is the function of the time-out decode logic to generate the appropriate trigger signals that are sent to the A-pulse generator 18 or the V-pulse generator 20 (FIG. 1). Further, an appropriate logic signal(s) is sent to the state logic 62 by the time-out decode logic 78 over signal line(s) 80 in order to notify the state logic that the respective trigger signals have been generated. It is to be understood that while FIG. 2 only shows one programmable timer 76, several such programmable timers may be used, as is required, in order to simultaneously keep track of multiple time intervals.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2 and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25–40 Khz for the basic clock rate C0 is adequate. This rate provides a basic time increment of 25–40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 2 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as a V-A Interval (VAI) state wherein a prescribed ventricular-to-atrial (V-A) interval is initiated. For purposes of the present invention, this V-A interval may be considered as the "atrial escape interval," or "AEI." As soon as the memory control 74 detects that the VAI state has been initiated, as evidenced by the "1000" appearing on the state bus 64, it retrieves from the memory 40 an appropriate data word, previously programmed into the memory 40 from the external programmer 48, or otherwise generated by the state logic 62, that defines the desired length of the AEI. This data word is sent to the programmable timer and sets the length of the time period that is to be measured during the VAI state.

The timer 76 is essentially just a counter that counts down (or counts up), using a specified clock signal, to the value specified in the data word. When the counting has been completed, and assuming that the counter has not been reset by the occurrence of a P-wave or other sensed event, the counter or timer 76 is said to have "timed-out," and an appropriate time-out signal is generated and sent to the time-out decode logic 78. The decode logic, in turn, recognizes that the current state of the system is the VAI state (as determined by monitoring the state bus 64), and therefore that the AEI has timed-out without any cardiac activity having been sensed. Hence, an A-pulse trigger signal is generated and sent to the A-pulse generator 18, so that the atrium can be stimulated. At the same time, an appropriate logic signal(s) is sent to the state logic 62 over the signal line(s) 80 to alert the state logic to the fact that the timer 76 has timed-out.

The state logic 62, in response to receiving the signal(s) from the time-out decode logic 78, and also in response to the current VAI state, triggers the next state of the prescribed sequence. For DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into the programmable timer 76. As soon as the timer 76 times out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, an AV-Interval state.

At the beginning of the AV-Interval state, another value is loaded into the programmable timer 76, or into an equivalent programmable timer, that defines the length of the pacemaker-defined AV interval, or "AVI." If the timer 76 times out without being reset, indicating that no R-wave has been sensed, the decode logic generates a V-pulse trigger signal, and notifies the state logic 62 of this event. The state logic, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a refractory (REF) state.

In the manner described above, the control system 26 assumes one state after another, thereby controlling the operation of the pacemaker. In general, a state is changed when the timer 76, or an equivalent timer, times out, or when a prescribed event occurs. Further, in accordance with the present invention, if a prescribed event occurs, e.g., the occurrence of a P-wave, then the next state may be a PV-Interval state. The PV-Interval state is the same as the AV-Interval state, described above, except that a different value is loaded into the programmable timer 76, which different value defines the length of the PV interval, or "PVI."

It is noted that the state of the control system could also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDD (dual-chamber pacing, dual-chamber sensing, dual mode (inhibited and triggered)); DDDR (dual-chamber pacing, dual-chamber sensing, dual mode (inhibited and triggered), rate-responsive); or VDI (ventricular chamber pacing, dual-chamber sensing, inhibited mode), for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 will not be presented herein because all such circuits may be conventional, or may be patterned after known circuits available in the art. Reference is made, for example, to U.S. Pat. No. 4,712,555, wherein a state machine-type of operation for a pacemaker is described; U.S. Pat. No. 4,788,980, wherein the various timing intervals used within the pacemaker and their interrelationship are more thoroughly described; and U.S. Pat. No. 4,944,298, wherein an atrial rate-based programmable pacemaker is described, including a thorough description of the operation of the state logic used to control such a pacemaker. The '555, '980 and '298 patents are incorporated herein by reference.

Figure 3:
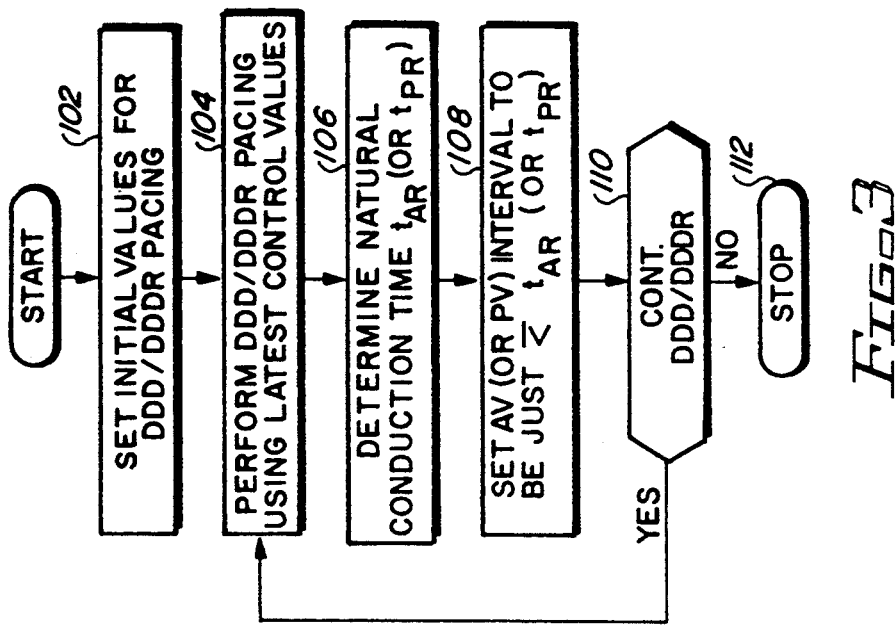
FIG. 3 is a flowchart illustrating the method of the present invention.

Of primary significance to the present invention is the manner in which the AV interval (or PV interval) is adaptively adjusted as a function of the measured natural conduction time of the patient. The manner in which this is done is illustrated in the flowchart of FIG. 3. In FIG. 3, as well as the other flowcharts presented herein, each main step of the method being described is illustrated as a "box" or "block." Reference numerals are assigned to each block of the flowchart to aid in the description of the invention that follows. Each step of the method, i.e., each block, may be readily carried out by those of skill in the art by programming appropriate "code" in the memory 40, which code causes the necessary control signals to be generated to carry out the desired steps. Equivalent techniques for generating the control signals needed to carry out the prescribed method or sequence may also, of course, be used.

As seen in FIG. 3, the method starts by setting the initial values needed by the pacemaker to carry out DDD or DDDR pacing (block 102). Such values are, for the most part, no different than those used when performing conventional DDD or DDDR pacing, and include such values as an initial pacing rate (from which an appropriate atrial escape interval is determined), an initial value for the AV interval, blanking period values, maximum pacing rate values, stimulation pulse amplitudes and widths, and the like. In accordance with the present invention, such initial values also include a minimum and maximum value for the AV (or PV) interval, plus a prescribed time difference between the natural conduction time of the patient and the pacemaker-defined AV (or PV) interval. In some embodiments of the invention, it may also be important to specify the difference between the AV interval and a PV interval, where the AV interval is the natural conduction time as measured from the delivery of an A-pulse to the subsequent occurrence of an R-wave, and the PV interval is the natural conduction time as measured from the occurrence of a P-wave to the subsequent occurrence of an R-wave.

Once the initial values needed to carry out DDD or DDDR pacing have been set, the specified DDD or DDDR pacing is carried out (block 104) in conventional manner, one cardiac cycle at a time, using the programmed values. At some point in a cardiac cycle associated with such DDD or DDDR pacing, an R-wave will occur; or a number of consecutive cardiac cycles will go by without the occurrence of an R-wave. Either event signals a need to determine the natural conduction time of the patient (block 106), so that an appropriate adjustment to the AV (or PV) interval of the pacemaker can be made, as needed (block 108).

The occurrence of an R-wave indicates the depolarization of the ventricles as a result of a natural or native conduction time that is shorter than the presently existing AV (or PV) interval of the pacemaker. Hence, such event indicates that the pacemaker-defined AV (or PV) interval needs to be decreased. Accordingly, as soon as an R-wave occurs, the natural or native conduction time of the patient, $t_{AR}$ or $t_{PR}$, is determined. Such natural conduction time is determined as the time interval between the most recent atrial activity, which would be either a P-wave or an A-pulse, and the R-wave. That is, the native or natural conduction time (note, as used herein, "native" and "natural" are used as synonyms) begins with the occurrence of atrial activity, and ends with the occurrence of an R-wave. If the most recent atrial activity was a P-wave, then the conduction time measured is $t_{PR}$. If the most recent atrial activity was an A-pulse, then the conduction time measured is $t_{AR}$.

If an R-wave fails to occur for a prescribed number of cardiac cycles, then that provides an indication that perhaps the natural conduction time has increased, and that there is a need to increase the AV (or PV) interval so that it is not too different than the natural conduction time.

In either event, once a determination is made that the natural conduction time has either decreased or increased (block 106), the AV (or PV) interval of the pacemaker is then set to a value that is just less than the determined natural conduction time. This is done by either decreasing the AV (or PV) interval when it appears that the natural conduction time has decreased (as is most often the case when an R-wave has been sensed), or by increasing the AV (or PV) interval when it appears that the natural conduction time may have increased (as is most often the case when an R-wave has not been sensed for a prescribed number of cardiac cycles).

After the AV (or PV) intervals have been set to be less than the determined conduction time $t_{AR}$ (or $t_{PR}$) at block 108, then a determination is made as to whether DDD or DDDR pacing is to continue (block 110). If not, then the method terminates (block 112). If so, then the method continues (block 104) by performing the DDD or DDDR pacing for the next cardiac cycle using the adjusted values of the AV (or PV) interval.

Figure 4:
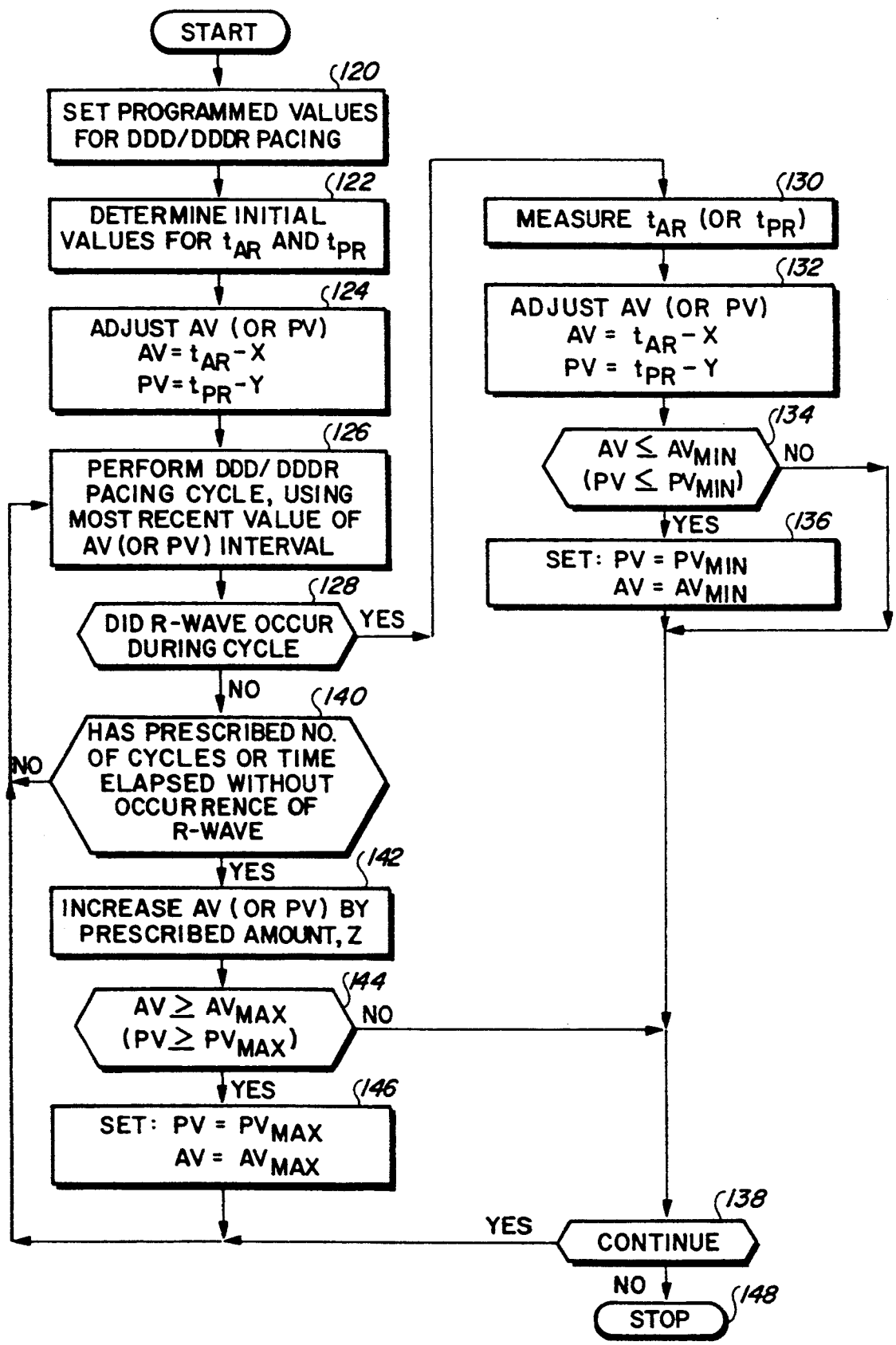
FIG. 4 is a more detailed flowchart illustrating the method of the present invention.

Turning next to FIG. 4, a more detailed flowchart is illustrated that shows the preferred technique for determining or measuring the natural conduction time of the patient (block 106 in FIG. 3), and adjusting the AV (or PV) intervals accordingly (block 108 in FIG. 3).

In FIG. 4, the programmed values needed to carry out DDD or DDDR pacing are programmed into the pacemaker in conventional manner (block 120). In accordance with the present invention, such programmed values include the number of cardiac cycles that must occur without an R-wave before the AV (or PV) interval is increased, the amount of such increase, an initial value for the natural conduction time $t_{AR}$ (or $t_{PR}$), or an indication of a technique for determining such initial values, the difference X and/or Y between the natural conduction times and the AV (or PV) intervals, and the like (block 122). Once the initial values of $t_{AR}$ or ($t_{PR}$) have been determined, then the value of the AV (or PV) interval is set to be a specified amount less than $t_{AR}$ or $t_{PR}$ (block 124).

With the AV (or PV) interval set to an initial value, the DDD or DDDR pacing cycle commences using such value, plus the other programmed values (block 126). If an R-wave is sensed during the pacing cycle (block 126), then that signals that the natural conduction time $t_{AR}$ (or $t_{PR}$) is shorter than the pacemaker-defined AV (or PV) interval. The occurrence of the R-wave indicates the end of the conduction time $t_{AR}$ (or $t_{PR}$), and thus permits a measurement of $t_{AR}$ (or $t_{PR}$) to be completed (block 130). Two different measurement techniques for determining $t_{AR}$ (or $t_{PR}$) are detailed more fully in FIGS. 5 or 6. The measured value of $t_{AR}$ (or $t_{PR}$) is then used as a basis for decreasing the AV (or PV) interval (block 132). The AV interval is set to $t_{AR}$-X, where X is a parameter having a programmable value, a fixed value, or an adaptive value based on a percentage of the heart rate. Similarly, the PV interval is set to $t_{PR}$-Y, where Y is a parameter having a programmable value, a fixed value, or an adaptive value based on a percentage of the heart rate.

As is described more fully below in conjunction with FIGS. 5 and 6, in some embodiments of the invention, $t_{PR}$ and $t_{AR}$ are measured separately, and separate values are programmed or otherwise determined for the parameters X and Y. Thus, in such embodiments, $t_{PR}$ and the resulting PV interval, and $t_{AR}$ and the resulting AV interval, are totally independent of each other. In other embodiments, one of $t_{AR}$ or $t_{PR}$ is determined, whichever happens to occur first, and the other is computed as a function of the measured value. In such embodiments, $t_{AR}$ is set to be a prescribed number of milliseconds greater than $t_{PR}$. In such embodiments, there is thus a prescribed relationship between $t_{AR}$ and $t_{PR}$ and the resulting AV and PV intervals. For most purposes relating to the description of the present invention, one of the AV (or PV) intervals, or one of the conduction times $t_{AR}$ (or $t_{PR}$), is all that is expressly referenced, and it is assumed that the other can be determined in an appropriate manner.

After the AV (or PV) interval has been set to its new value based on the most recent measured value of $t_{AR}$ (Or $t_{PR}$) (block 132), a determination is made as to whether the new value of the AV (or PV) interval is less than or equal to a programmed minimum value for the AV (or PV) interval, $AV_{MIN}$ (or $PV_{MIN}$) (block 134). If so, then the AV (or PV) interval is set to $AV_{MIN}$ (or $PV_{MIN}$). If not, then the AV (or PV) interval maintains the value previously determined. If DDD (or DDDR) pacing is to continue (block 138), then the next cycle of such pacing continues using the newly set value of the AV (or PV) interval (bock 126).

Should an R-wave not occur during the pacing cycle (block 128), then a determination is next made (block 140) as to whether a prescribed (programmed) number of cardiac cycles have occurred without the occurrence of an R-wave. If not, then the next cycle begins (block 126). If yes, then that indicates that perhaps the natural conduction time has increased, and that the AV (or PV) interval should also be increased to keep the difference between such natural conduction time and the AV (or PV) intervals to a minimum. Accordingly, the AV (or PV) interval is increased by a prescribed amount, Z (block 142). The value Z may be a fixed value, a programmable value, an adaptive value based on a percentage of heart rate, or a value based on the current AV interval. After the AV (or PV) interval has been increased, a determination is made as to whether the new value of the AV (or PV) interval is greater than or equal to a programmed maximum value for the AV (or PV) interval, $AV_{MAX}$ (or $PV_{MAX}$) (block 144). If so, then the AV (or PV) interval is set to $AV_{MAX}$ (or $PV_{MAX}$). If not, then the AV (or PV) interval maintains the value previously determined (at block 142). If DDD (or DDDR) pacing is to continue (block 138), then the next cycle of such pacing continues using the newly set value of the AV (or PV) interval (bock 126).

The number of cardiac cycles that must occur without the occurrence of an R-wave before the AV (or PV) interval is increased is preferably a programmable number, and may typically be anywhere from 8 to 128 cycles. Alternatively, a specific time interval may be specified, 2–10 minutes, that must elapse without the occurrence of an R-wave before the AV (or PV) interval is increased. The amount Z by which the AV (or PV) interval is incrementally increased is also preferably a programmable value, but could be a fixed value, or an adaptive value. Typical values for Z range from 5–30 msec.

Figure 5:
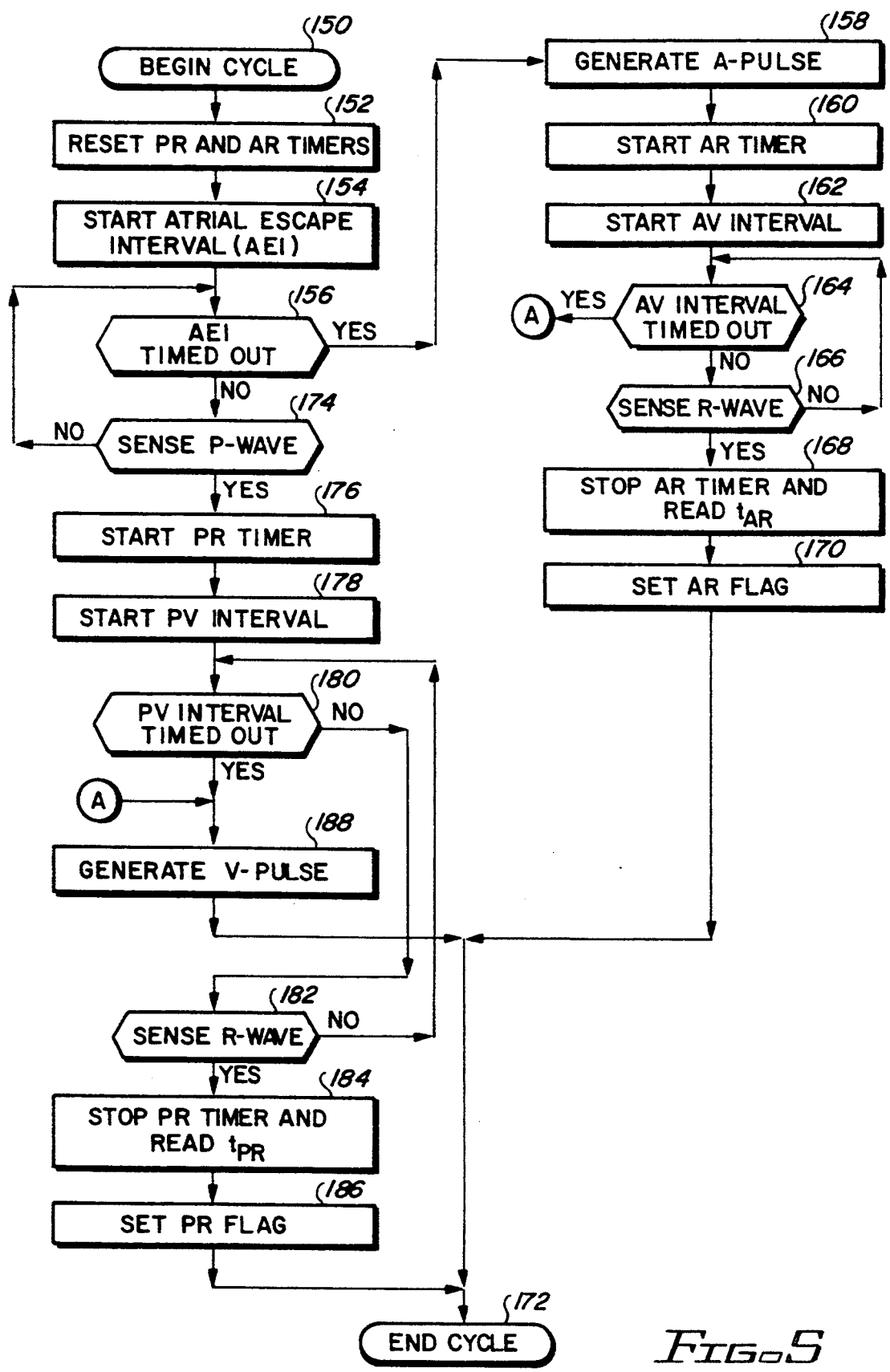
FIG. 5 is a flowchart that illustrates one technique for measuring the natural conduction time of a patient.

Referring next to FIG. 5, a flowchart is shown that illustrates one technique for measuring the natural conduction times, $t_{AR}$ and $t_{PR}$, during one or more cardiac cycles of the heart. The technique shown in FIG. 5 makes an independent measurement of both $t_{AR}$ and $t_{PR}$. As seen in FIG. 5, at the beginning of the cardiac cycle (block 150), a PR timer and an AR timer are reset (block 152). Such timers, as well as the other timers referenced herein, may be implemented in hardware or software within the control system 26 (FIGS. 1 and 2).

After resetting such timers, an atrial escape interval (AEI) begins (block 154). If a P-wave is not sensed during the AEI (blocks 156, 174), then an A-pulse is generated (block 158), and the AR timer commences (block 160). Also, the AV interval begins (block 162). If an R-wave occurs during the AV interval (blocks 164, 166), then the AR timer is stopped, and the value of the AR timer represents a measure of the conduction time $t_{AR}$ (block 168). An AR flag is then set (block 170), and the cardiac cycle ends (block 172), having determined $t_{AR}$ during the cycle.

If the AV interval times out without detecting an R-wave (block 164), then a V-pulse is generated (block 188), and the cardiac cycle ends (block 172), having made no determination of either $t_{AR}$ or $t_{PR}$ during the cycle. Thus, the value of $t_{AR}$ and/or $t_{PR}$ used at the beginning of the next cardiac cycle is retained as the conduction time value used for the preceding cardiac cycle.

Should a P-wave be sensed before the AEI times out (blocks 156, 174), than the PR timer is started (block 176). Also, the PV interval is started (block 178). If an R-wave occurs during the PV interval (blocks 189, 182), then the PR timer is stopped, and the value of the PR timer represents a measure of the conduction time $t_{PR}$ (block 184). A PR flag is then set (block 186), and the cardiac cycle ends (block 172), having determined $t_{PR}$ during the cycle.

It is noted that the AR and PR flags that are set during the cardiac cycle, depending upon whether a P-wave or an A-pulse occurs, may be used during the operation of the pacemaker to steer the adjustment of the AV interval (if the AR flag is set), or the PV interval (if the PR flag is set).

Figure 6:
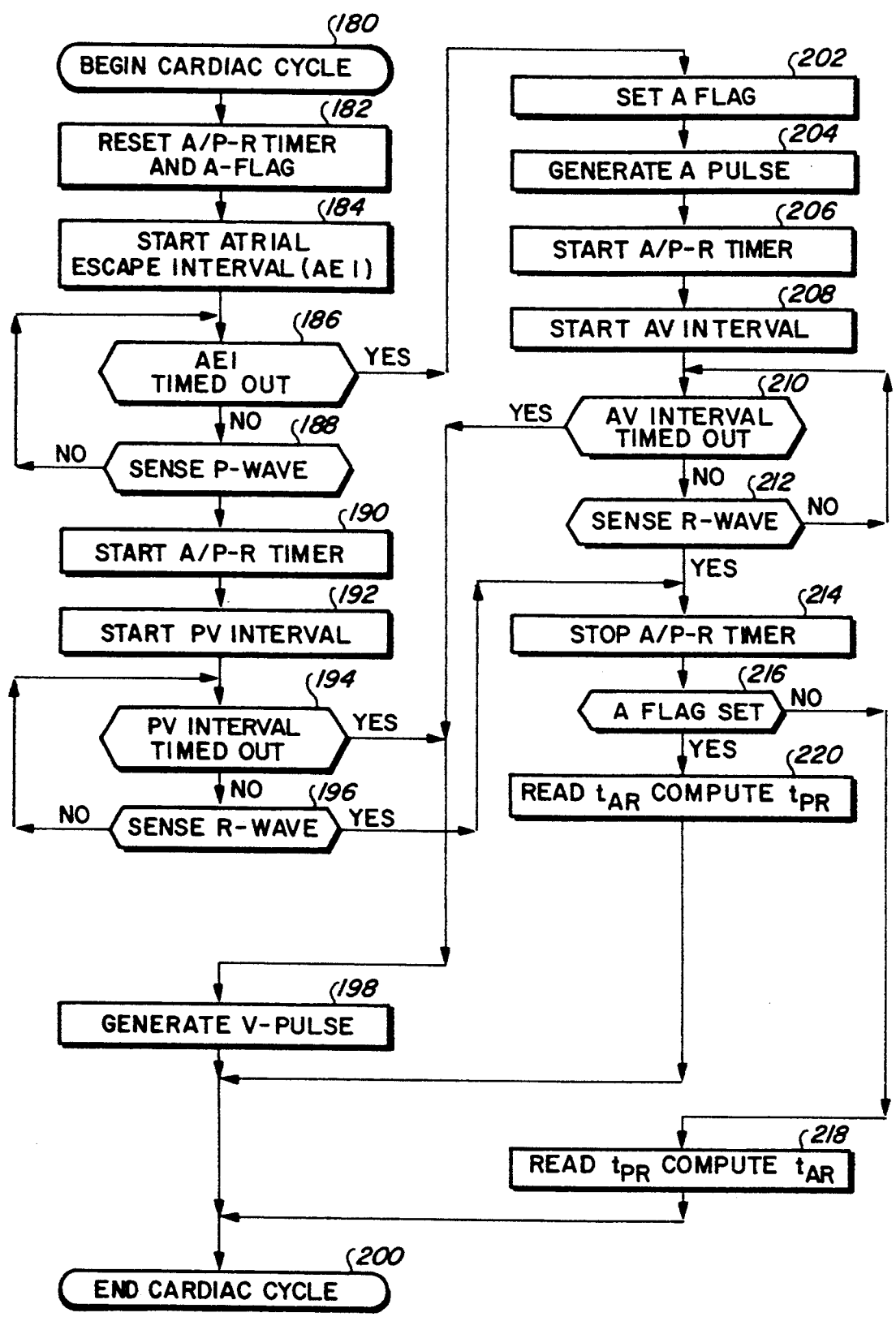
FIG. 6 is a flowchart that illustrates another embodiment for determining the natural conduction time of a patient, wherein one of the PR or AR conduction time intervals is measured, and the other is set as a prescribed difference from the measured value.
Figure 6:
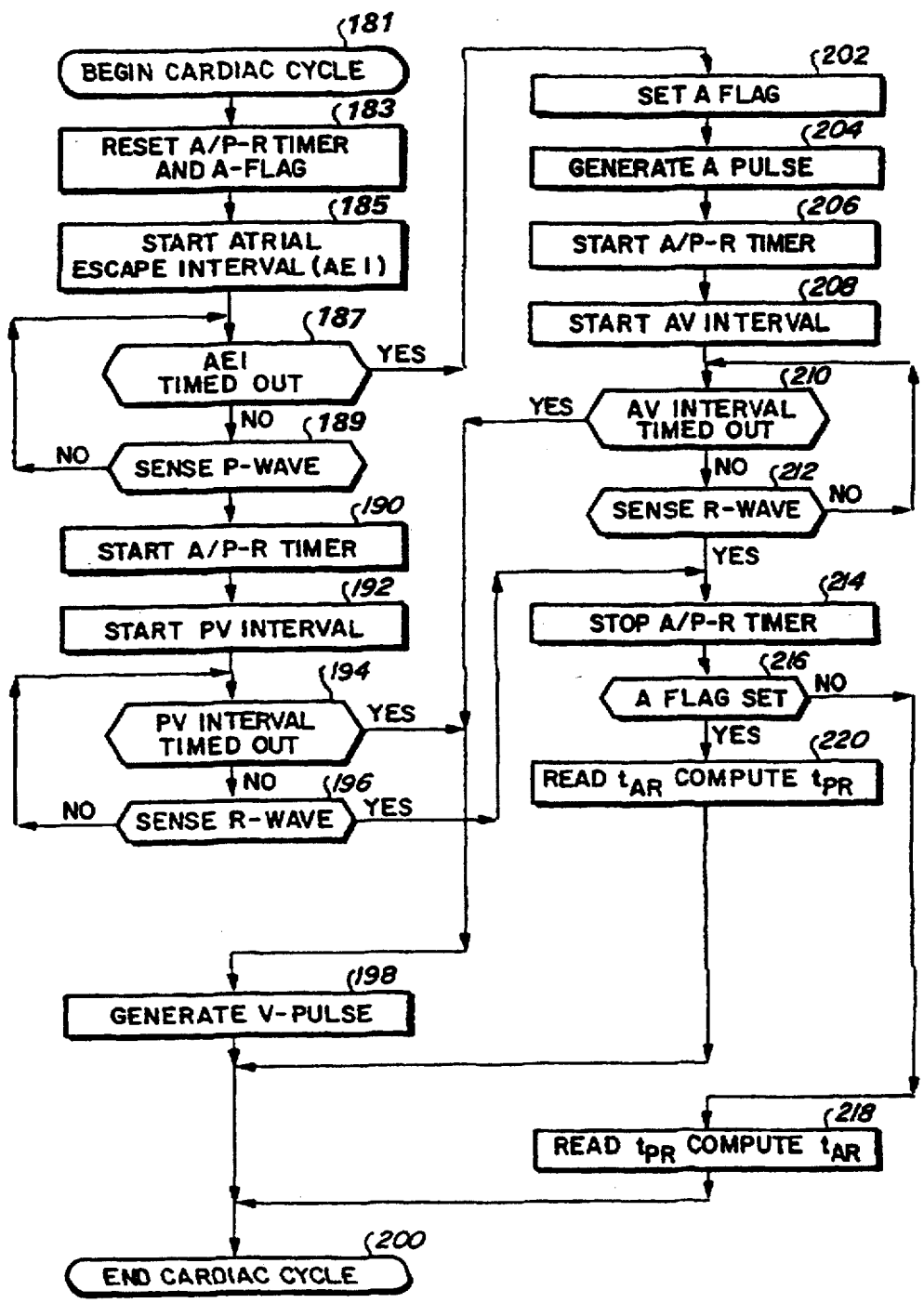

Turning next to FIG. 6, a flowchart of another embodiment or technique for determining the natural conduction time of a patient is illustrated. The technique shown in FIG. 6 determines just one of $t_{AR}$ or $t_{PR}$, and the other is set as a prescribed difference from the measured value. Thus, as seen in FIG. 6, once the cardiac cycle begins (block 180), a single timer, designated as the A/P-R Timer, is reset, as is a single flag, designated the A-Flag (block 182). The atrial escape interval (AEI) is started (block 184), and a determination is made as to whether a P-wave is sensed before the timing-out the AEI (blocks 186, 188). If so, then the A/P-R Timer is started (block 190), and the PV interval is started (block 192). While the PV interval is timing-out, a determination is made as to whether an R-wave occurs (blocks 194, 196). If an R-wave does occur during the PV interval, then the A/P-R Timer is stopped (block 214), and a determination is made as to whether the A-Flag is set (block 216). If the A/P-R Timer is not set, then that signals that the A/P-R Timer contains the $t_{PR}$ value, which $t_{PR}$ value may be read from the A/P-R Timer, and the $t_{AR}$ value may be computed therefrom. Typically, $t_{AR}$ is computed as the measured value of $t_{PR}$ less $Y_A$ msec, where $Y_A$ may be a fixed value, a programmed value, or an adaptive value based on a percentage of the heart rate. The cardiac cycle is then completed (block 200) having measured a value of $t_{PR}$ and computed a value of $t_{AR}$ during the cycle.

If the PV interval times out without sensing an R-wave (blocks 194, 196), then a V-pulse is generated (block 198), and the cardiac cycle terminates (block 200) without having determined a new value for the conduction time $t_{AR}$ or $t_{PR}$. Hence, the next cardiac cycle starts using the previously determined values of $t_{AR}$ or $t_{PR}$.

If the AEI times out without having sensed a P-wave (blocks 186, 188), then the A-Flag is set (block 202), and an A-pulse is generated (block 204). Also, the A/P-R Timer is started (block 206), and the AV interval is started (block 208). While the AV interval is timing-out, a determination is made as to whether an R-wave occurs (blocks 210, 212). If an R-wave does occur during the AV interval, then the A/P-R Timer is stopped (block 214), and a determination is made as to whether the A-Flag is set (block 216). If the A-Flag is set, then that signals that the A/P-R Timer contains the $t_{AR}$ value, which $t_{AR}$ value may be read from the A/P-R Timer, and the $t_{PR}$ value may be computed therefrom. Typically, $t_{PR}$ is computed as the measured value of $t_{AR}$ minus $Y_B$ msec, where $Y_B$ may be a fixed value, a programmed value, or an adaptive value based on a percentage of the heart rate. The cardiac cycle is then completed (block 200) having measured a value of $t_{AR}$ and computed a value of $t_{PR}$ during the cycle.

If the AV interval times out without sensing an R-wave (blocks 210, 212), then a V-pulse is generated (block 198), and the cardiac cycle terminates (block 200) without having determined a new value of the conduction times $t_{AR}$ or $t_{PR}$. Hence, the next cardiac cycle starts using the previously determined values of $t_{AR}$ or $t_{PR}$.

Thus it is seen that the present invention provides an implantable pacemaker, and method of operating such a pacemaker, that stimulates cardiac tissue at a time in the cardiac cycle that is just prior to when natural depolarization of the cardiac tissue would otherwise cause a cardiac contraction.

As further described above, it is seen that the invention provides a dual-chamber pacemaker, and method of operating such a dual-chamber pacemaker, that automatically adjusts the pacemaker-defined AV interval to a value that is just less than the natural conduction time of the patient. Such action advantageously assures that a V-pulse is generated and delivered to the ventricular muscle tissue at a time in the cardiac cycle when such ventricular muscle is not refractory (i.e., prior to the natural depolarization of the ventricular tissue), while still maintaining the approximate cardiac timing set by the natural conduction time, thereby maximizing the cardiac output of the patient.

As also described above, it is seen that the invention provides a dual-chamber pacemaker, and method of operating such a pacemaker, that decreases the pacemaker-defined AV interval in response to sensing an R-wave (which sensed R-wave evidences a shortened natural conduction time), and that automatically increases the pacemaker-defined AV interval in prescribed increments in response to not sensing an R-wave for a prescribed number of consecutive cardiac cycles (which failure to sense any R-waves may evidence a lengthening of the natural conduction time). Thus, advantageously, the pacemaker-defined AV interval is most always set to a value that is just somewhat less than the natural conduction time, regardless of whether the natural conduction time is increasing or decreasing, and the cardiac output of the patient is maximized.

While the invention herein disclosed has been described by means of specific embodiments and applications thereof, numerous modifications and variations could be made thereto by those skilled in the art without departing from the scope of the invention set forth in the claims.

What is claimed is:

1. A dual-chamber pacemaker providing atrioventricular pacing in order to increase cardiac output in a patient suffering from a cardiomyopathy, comprising:

an atrial channel and a ventricular channel;

an atrial sense amplifier that senses a P-wave in the atrial channel, said P-wave representing natural atrial activity;

a ventricular sense amplifier that senses an R-wave in the ventricular channel, said R-wave representing natural ventricular activity;

pulse generator means for generating an atrial stimulation pulse (A-pulse) in the atrial channel in the absence of a sensed P-wave by said atrial sense amplifier within an atrial escape interval, and a ventricular stimulation pulse (V-Pulse) in the ventricular channel in the absence of a sensed R-wave by said ventricular sense amplifier within an AV time interval;

a control system that defines said AV time interval and said atrial escape interval, said AV time interval beginning upon the sensing of a P-wave or the generation of an A-pulse, whichever event occurs first in the atrial channel, and said atrial escape interval beginning upon the sensing of an R-wave or the generation of a V-pulse, whichever event occurs first in the ventricular channel; and timing means as part of said control system for measuring a conduction time interval as the time period between atrial activity in the atrial channel and the sensing of an R-wave in the ventricular channel, and for automatically setting said AV time interval to a value that for ventricular pacing is always less than the measured conduction time interval by a prescribed amount, said atrial activity comprising the generation of an A-pulse or the sensing of a P-wave, whichever event occurs first, in the atrial channel;

whereby, in the absence of a decreasing conduction time interval, said pulse generator means generates said V-pulse in the ventricular channel prior to the occurrence of an R-wave, thereby providing ventricular pacing for increasing cardiac output; and further whereby, in the presence of a decreasing conduction time interval, said AV time interval is automatically adjusted to a value less than the shortest conduction time interval.

2. The dual-chamber pacemaker, as set forth in claim 1, wherein said timing means of said control system further automatically increases said AV time interval by a prescribed amount in the event a prescribed number of consecutive cardiac cycles occur without an R-wave being sensed by said ventricular sense amplifier; a cardiac cycle comprising the time period between consecutive atrial activity, whereby said AV time interval does not remain adjusted to a value less than the shortest conduction time interval in the absence of sensed R-waves for a period of time longer than said prescribed number of cardiac cycles.

3. The dual-chamber pacemaker, as set forth in claim 2, further comprising a memory circuit coupled to said control system, said memory circuit having prescribed minimum and maximum AV interval values stored therein, said minimum and maximum AV interval values being usable by said control system to limit the adjustment of said AV time interval between said minimum and maximum AV interval values.

4. The dual-chamber pacemaker, as set forth in claim 3, wherein said control system comprises a state logic circuit that changes states in response to the occurrence of prescribed events, said prescribed events including the timing-out of specified time intervals, and the sensing of activity in the atrial or ventricular channels.

5. The dual-chamber pacemaker, as set forth in claim 3, wherein said control system comprises a programmable timer circuit and a clock circuit, said programmable timer circuit having a time interval value loaded therein, said clock circuit generating a clock signal that counts said programmable timer circuit for the number of counts represented by said time interval value, whereupon said programmable timer circuit issues a time-out signal; said time interval value being adaptively changed by logic circuits within said control system to represent the AV time interval, whereby said programmable timer circuit defines said AV time interval.

6. A dual-chamber implantable pacemaker programmed to operate in a DDD or DDDR mode of operation so as to generate a ventricular stimulation pulse (V-pulse) during a given cardiac cycle prior to natural ventricular activity, yet at a time delayed sufficiently from any preceding atrial activity to assure efficient cardiac output, said pacemaker comprising:
sensing means for sensing P-waves and R-waves;
stimulation means for generating V-pulses and A-pulses;
measurement means for measuring the natural conduction time, $t_{PR}$, or $t_{AR}$, of a heart to which the pacemaker is coupled, where $t_{PR}$ represents the natural conduction time following a natural atrial event (P-wave), and $t_{AR}$ represents the natural conduction time of the heart following an atrial stimulation pulse (A-pulse); and
timing means for automatically setting a PV interval for use by said pacemaker following a P-wave, and an AV interval for use by said pacemaker following an A-pulse, to a prescribed amount less than said natural conduction time, $t_{PR}$ or $t_{AR}$, respectively, said PV and AV intervals being used by said timing means to define the time period between a P-wave and a V-pulse, and between an A-pulse and a V-pulse, respectively, during the operation of said pacemaker.

7. The dual-chamber implantable pacemaker, as set forth in claim 6, wherein said timing means automatically adjusts said PV and AV intervals to make them a prescribed amount less than the PV or AV interval used by said pacemaker in a most recent cardiac cycle in the event an R-wave is sensed during said most recent pacing cycle.

8. The dual-chamber implantable pacemaker, as set forth in claim 7, wherein said timing means further automatically adjusts said PV and AV intervals to make them a prescribed amount greater than the PV or AV interval used by said pacemaker in a most recent cardiac cycle, up to a predetermined maximum PV or AV interval, in the event no R-wave is sensed for a specified number of consecutive prior cardiac cycles.

9. The dual-chamber implantable pacemaker, as set forth in claim 6, wherein said measurement means includes means for measuring one of said $t_{PR}$ or $t_{AR}$ natural conduction times, depending upon which of said A-pulse or P-wave occurs first, and computing the other of said $t_{PR}$ or $t_{AR}$ natural conduction times as a function of said measured one of said $t_{PR}$ or $t_{AR}$ natural conduction times.

10. The dual-chamber implantable pacemaker, as set forth in claim 9, wherein said means for computing the other of said $t_{PR}$ or $t_{AR}$ natural conduction times once one has been measured comprises means for defining $t_{AR}$ to be a prescribed amount greater than $t_{PR}$, whereby once one of said $t_{PR}$ or $t_{AR}$ natural conduction times has been measured, the other of said $t_{PR}$ or $t_{AR}$ natural conduction times is computed to be less than or greater than the measured value of $t_{PR}$ or $t_{AR}$ by said prescribed amount.

11. The dual-chamber implantable pacemaker, as set forth in claim 6, wherein said measurement means includes means for measuring both $t_{PR}$ and $t_{AR}$, where $t_{PR}$ is measured as the time interval between the occurrence of a P-wave and a subsequent R-wave, and $t_{AR}$ is measured as the time interval between the generation of an A-pulse and a subsequent R-wave.

12. The dual-chamber implantable pacemaker, as set forth in claim 6, wherein said timing means sets the PV interval to be a first prescribed amount less than $t_{PR}$, and sets the AV interval to be a second prescribed amount less than $t_{AR}$.

13. The dual-chamber implantable pacemaker, as set forth in claim 12, wherein said first prescribed amount is the same as said second prescribed amount, whereby the difference between said PV interval and said AV interval is the same as the difference between $t_{AR}$ and $t_{PR}$.

14. The dual-chamber implantable pacemaker, as set forth in claim 12, wherein said first prescribed amount and said second prescribed amount are computed as a function of the most recent measured values of $t_{PR}$ and $t_{AR}$, respectively.

15. A dual chamber pacemaker comprising:
means for sensing and pacing in both an atrial and ventricular channel;
timing means for setting an AV interval, said AV interval comprising the maximum time period allowed by the pacemaker between atrial channel activity, which atrial channel activity includes sensing or pacing in the atrial channel, and pacing in the ventricular channel;
measurement means for measuring a first time interval as the time interval between atrial channel activity and sensing in the ventricular channel;
adjustment means for automatically setting the AV interval of said pacemaker to a value that for pacing in the ventricular channel is always less than the most recently measured first time interval; and
control means for pacing in the ventricular channel at the conclusion of said AV interval in the event that no sensing occurs in the ventricular channel during said AV interval, whereby ventricular pacing is provided.

16. The dual-chamber pacemaker, as set forth in claim 15, wherein said measurement means measures said first time interval each time that sensing occurs in the ventricular channel.

17. The dual-chamber pacemaker, as set forth in claim 15, wherein said adjustment means also increases said AV interval by a specified amount in the event that no sensing occurs in the ventricular channel for a prescribed number of cardiac cycles, where a cardiac cycle comprises the consecutive occurrence of atrial channel activity followed by pacing in the ventricular channel.

18. A method of operating a dual-chamber implantable pacemaker to provide ventricular stimulation pulses at a time within a cardiac cycle that is just prior to when a natural ventricular contraction would occur, said implantable pacemaker including means for sensing natural atrial contractions (P-waves), means for sensing natural ventricular contractions (R-waves), means for generating atrial stimulation pulses (A-pulses), means for generating ventricular stimulation pulses (V-pulses), and timing means for defining an AV interval that commences with the generation of an A-pulse, and a PV interval that commences with the sensing of a P-wave, said method comprising:

(a) electronically measuring a first time interval within a given cardiac cycle that comprises the time between an atrial event and an R-wave, said atrial event comprising either an A-pulse or a P-wave, whichever event occurs first in the given cardiac cycle;

(b) automatically setting said AV interval to be equal to said first time interval less a first prescribed amount;

(c) automatically setting said PV interval to be equal to said first time interval less a second prescribed amount; and (d) issuing a V-pulse at the conclusion of said AV interval, in the event an A-pulse has first been generated, or at the conclusion of said PV interval, in the event a P-wave has first been sensed; whereby said V-pulse is always generated at the conclusion of said AV or PV interval following said atrial event.

19. The method, as set forth in claim 18, wherein steps (a) to (c) are performed periodically at a prescribed interval, and step (d) is performed every cardiac cycle using the most recent AV or PV interval set by steps (b) and (c).

20. The method, as set forth in claim 19, wherein the prescribed interval at which steps (a)-(c) are performed comprises an interval defined by the occurrence of a programmed number of consecutive cardiac cycles.

21. The method, as set forth in claim 18, wherein steps (a) to (c) are performed during each cardiac cycle in which an R-wave occurs.

22. The method, as set forth in claim 21, further including increasing said AV and PV intervals by a third prescribed amount up to a maximum AV and PV interval in the event a predetermined number of consecutive cardiac cycles occurs without the occurrence of an R-wave.

23. In a dual-chamber implantable pacemaker programmed to operate in a DDD or DDDR mode of operation, a method of operating said pacemaker when coupled to a heart of a patient so as to generate a ventricular stimulation pulse (V-pulse) during a given cardiac cycle prior to natural ventricular activity, yet at a time delayed sufficiently from any preceding atrial activity to assure efficient cardiac output, said pacemaker including means for sensing P-waves and R-waves, and means for generating V-pulses and A-pulses, said method comprising the steps of:

(a) determining the natural conduction time of the heart, $t_{PR}$ or $t_{AR}$, where $t_{PR}$ represents the natural conduction time following a natural atrial event (P-wave), and $t_{AR}$ represents the natural conduction time of the heart following an atrial stimulation pulse (A-pulse);

(b) automatically setting a PV interval, for use by said pacemaker following a P-wave, and an AV interval, for use by said pacemaker following an A-pulse, to a prescribed amount less than said natural conduction time, $t_{PR}$ or $t_{AR}$, respectively;

(c) performing at least one pacing cycle in said DDD or DDDR mode of operation using the PV and AV intervals to define the time period between an atrial event and the generation of a V-pulse;

(d) automatically adjusting said PV and AV intervals to make them a prescribed amount less than the PV or AV interval used most recently by said pacemaker in the event an R-wave is sensed during said at least one pacing cycle; and (e) automatically adjusting said PV and AV intervals to make them a prescribed amount greater than the PV or AV interval used most recently by said pacemaker, up to a predetermined maximum PV or AV interval, in the event no R-wave is sensed for a specified number of cardiac cycles.

24. The method, as set forth in claim 23, wherein step (a) comprises measuring one of said $t_{PR}$ or $t_{AR}$ natural conduction times, depending upon which of said A-pulse or P-wave occurs first, and computing the other of said $t_{PR}$ or $t_{AR}$ natural conduction times as a function of said measured one of said $t_{PR}$ or $t_{AR}$ natural conduction times.

25. The method, as set forth in claim 24, wherein computing the other of said $t_{PR}$ or $t_{AR}$ natural conduction times once one has been measured comprises defining $t_{AR}$ to be a prescribed amount greater than $t_{PR}$, whereby once one of said $t_{PR}$ or $t_{AR}$ natural conduction times has been measured, the other of said $t_{PR}$ or $t_{AR}$ natural conduction times is computed to be less than or greater than the measured value of $t_{PR}$ or $t_{AR}$ by said prescribed amount.

26. The method, as set forth in claim 23, wherein step (a) comprises measuring both $t_{PR}$ and $t_{AR}$, where $t_{PR}$ is measured as the time interval between the occurrence of a P-wave and a subsequent R-wave, and $t_{AR}$ is measured as the time interval between the generation of an A-pulse and a subsequent R-wave.

27. The method, as set forth in claim 23, wherein step (b) comprises setting the PV interval to be a first prescribed amount less than $t_{PR}$, and setting the AV interval to be a second prescribed amount less than $t_{AR}$.

28. The method, as set forth in claim 27, wherein said first prescribed amount is the same as said second prescribed amount, whereby the difference between said PV interval and said AV interval is the same as the difference between $t_{AR}$ and $t_{PR}$.

29. The method, as set forth in claim 27, wherein said first prescribed amount and said second prescribed amount are computed as a function of the most recent measured values of $t_{PR}$ and $t_{AR}$, respectively.

30. A method of providing ventricular pacing in order to increase cardiac output in a cardiomyopathy patient, such patient having a dual-chamber pacemaker, said pacemaker including means for sensing and pacing in both an atrial and ventricular channel, and timing means for setting an AV interval, said method comprising the steps of:

(a) measuring a first time interval as the time interval between atrial channel activity and sensing in the ventricular channel for determining a natural conduction time, said atrial channel activity comprising sensing or pacing in the atrial channel;

(b) automatically setting the AV interval of said pacemaker to a value that is a prescribed amount less than the natural conduction time, where said AV interval defines the time interval between atrial channel activity and pacing in the ventricular channel; and (c) pacing in the ventricular channel at the conclusion of said AV interval.

31. The method, as set forth in claim 30, further comprising the step of:

(d) adjusting said AV interval to a value that is said prescribed amount less than the time interval between the most recent atrial channel activity and sensing in the ventricular channel in the event that sensing occurs in the ventricular channel during said AV interval.

32. The method, as set forth in claim 31, further comprising the step of:

(e) increasing said AV interval by a specified amount in the event that no sensing occurs in the ventricular channel for a prescribed number of cardiac cycles, where a cardiac cycle comprises the consecutive occurrence of atrial channel activity followed by pacing in the ventricular channel.

33. A dual-chamber pacemaker for controlling ventricular pacing in order to increase cardiac output in a patient suffering from a cardiomyopathy by preemptively stimulating the ventricular channel comprising:

an atrial channel and a ventricular channel;

an atrial sense amplifier that senses a P-wave in the atrial channel, said P-wave representing natural atrial activity;

a ventricular sense amplifier that senses an R-wave in the ventricular channel, said R-wave representing natural ventricular activity;

pulse generator means for generating a ventricular stimulation pulse (V-Pulse) in the ventricular channel and an atrial stimulation pulse (A-pulse) in the atrial channel, the sensing of a P-wave or the generating of an A-pulse, whichever occurs first, comprising atrial activity; and timing means for defining an AV time interval as the time interval between atrial activity and the generation of a V-pulse, said timing means further for measuring a natural conduction time interval as the time period between atrial activity and the sensing of an R-wave, and for automatically setting said AV time interval to a value that is less than said natural conduction time interval, whereby said pulse generator generates said V-pulse prior to the occurrence of natural ventricular activity for preemptively stimulating the ventricular channel to thereby increase cardiac output.

34. The dual-chamber pacemaker of claim 33, further comprising means for setting the AV interval to a value that, for ventricular pacing, is always less than the natural conduction time interval by a prescribed amount.

* * * * *

UNITED STATES PATENT AND TRADEMARK OFFICE
CERTIFICATE OF CORRECTION

PATENT NO. : 5,340,361
DATED : August 23, 1994
INVENTOR(S) : Jason A. Sholder

It is certified that error appears in the above-identified patent and that said Letters Patent is hereby corrected as shown below:

Drawings,
Sheet 5, FIG. 6, replace reference numerals "180", "182", "184", "186", and "188" with reference numerals -- 181 --, -- 183 --, -- 185 --, -- 187 --, and -- 189 --, respectively, as depicted in the attached substitute formal Sheet 5, FIG. 6.

Title page,
Correct the title and column 1, lines 2-5 to read -- IMPLANTABLE PACEMAKER HAVING AV INTERVAL ADAPTIVELY SHORTENED TO ASSURE VENTRICULAR PACING --;

Column 10,
Line 29, replace "78" with -- 73 --;

Column 11,
Line 57, replace "62" with -- 60 --;

Column 12,
Line 1, replace "state registers 62" with -- state registers 60 --;

Column 14,
Line 50, replace "126" with -- 128 --;

Column 15,
Lines 28 and 53, replace "bock" with -- block --;

Column 16,
Line 30, replace "189" with -- 180 --;
Line 49, replace "180" with -- 181 --;
Line 51, replace "182" with -- 183 --;
Line 52, replace "184" with -- 185 --;
Line 54, replace "186, 188" with -- 187, 189 --;
Line 65, replace "less" with -- plus --; and

UNITED STATES PATENT AND TRADEMARK OFFICE
CERTIFICATE OF CORRECTION

PATENT NO. : 5,340,361
DATED : August 23, 1994
INVENTOR(S) : Jason A. Sholder

It is certified that error appears in the above-identified patent and that said Letters Patent is hereby corrected as shown below:

Column 17,
Line 11, replace "186, 188" with -- 187, 189 --.

Signed and Sealed this

Fifth Day of February, 2002

Attest:

Attesting Officer

JAMES E. ROGAN
Director of the United States Patent and Trademark Office